United States Patent [19]

McManus et al.

[11] Patent Number: 4,740,615
[45] Date of Patent: Apr. 26, 1988

[54] PROCESS FOR PURIFIED AMINO ACIDS

[75] Inventors: James W. McManus, Leesburg; Larry D. Forshey, Albany, both of Ga.

[73] Assignee: Merck & Co., Inc., Rahway, N.J.

[21] Appl. No.: 924,393

[22] Filed: Oct. 29, 1986

[51] Int. Cl.⁴ .............................................. C07C 99/12
[52] U.S. Cl. ................................... 562/446; 562/444; 562/445; 562/443
[58] Field of Search ................ 562/443, 444, 445, 446

[56] References Cited

U.S. PATENT DOCUMENTS

| | | | |
|---|---|---|---|
| 3,551,107 | 12/1970 | Hrdina | 562/443 |
| 3,972,918 | 8/1976 | Stanley et al. | 562/443 |
| 4,290,893 | 9/1981 | Hare et al. | 562/443 |
| 4,496,703 | 1/1985 | Steinmetzer | 562/444 |
| 4,584,399 | 4/1986 | Portat | 562/443 |
| 4,584,400 | 4/1986 | Otani et al. | 562/444 |

FOREIGN PATENT DOCUMENTS 147974 10/1985 European Pat. Off. ............ 562/443
154343 11/1985 Japan .................................. 562/443

Primary Examiner—James H. Reamer
Attorney, Agent, or Firm—Alice O. Robertson; Michael D. Sudol

[57] ABSTRACT

A process for the recovery in substantially pure form of an amino acid represented by the formula

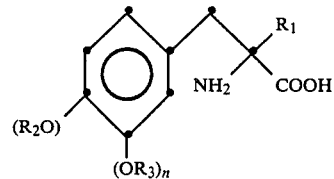

from an aqueous production mixture by a low pressure temperature gradient chromatographic process is described.

14 Claims, No Drawings

PROCESS FOR PURIFIED AMINO ACIDS

The present invention is directed to a process adaptable for obtaining lipophilic amino acids in substantially pure form on a large scale.

BACKGROUND OF THE INVENTION

Lipophilic amino acids such as phenylalanine, and substituted phenylalanines such as the natural occurring tyrosine and L-dopa (3-hydroxy-L-tyrosine), and the unnatural compounds such as the drug methyldopa, (L-3-(3,4-dihydroxyphenyl)-2-methyl-alanine), are important compounds for health and well-being, and are produced on a large scale. The by-products formed in the chemical manufacturing processes as well as in the production methods from natural sources such as fermentation or protein hydrolysis are such as to generally require costly separation procedures. Moreover, the procedures generally use organic solvents which are undesirable from health and environmental considerations. In some production procedures, the desired amino acid may be obtainable in reasonably pure form but is accompanied by loss of a portion thereof in the mother liquor. Recovery of the product from the mother liquor also is generally a costly separation procedure. Thus, a simple cost-effective recovery method which in addition, obviates the need for organic solvents is desirable.

STATEMENT OF THE INVENTION

According to the present invention it has been discovered that lipophilic amino acids such as phenylalanine and substituted phenylalanine may be recovered from various production mixtures containing such amino acids by adsorbing the mixture at or near the isoelectric pH of the amino acids on a non-ionic polymeric adsorbent and thereafter selectively desorbing by eluting employing gradient temperature at a low pressure.

DETAILED DESCRIPTION OF THE INVENTION

In the method of the present invention, at least one amino acid having the formula

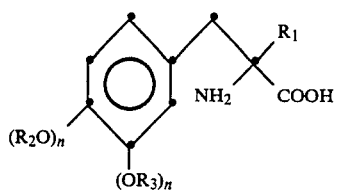

wherein $R_1$, $R_2$ and $R_3$ are independently hydrogen, lower alkyl, lower haloalkyl and aryl and each n is independently 0 or 1, is recovered from an aqueous mixture containing such amino acid or acids by adsorbing said amino acid or acids at or near its isoelectric PH on a non-ionic polymer resin and thereafter eluting the acid or acids with deionized water and using a temperature gradient when it is desired to recover two or more amino acids.

The aqueous mixture from which substantially pure amino acid or acids are to be recovered according to the present invention may arise from an organic synthesis, a fermentation process, or a protein or peptide hydrolysis, and will contain at least one amino acid of the foregoing formula and may also contain other organic and inorganic matter including other amino acids, peptide hydrolysates, organic compounds and inorganic salts.

The process for recovering at least one amino acid conforming to the general formula in substantially pure from comprises:

(1) adjusting the PH of the aqueous mixture to or near the isoelectric PH of the desired amino acid or acids;

(2) loading the mixture on a column of non-ionic polymer resin and allowing the aqueous solution to percolate through the column, whereby the amino acid or acids are adsorbed (and discarding the filtrate);

(3) displacing the entrained or adsorbed inorganic salts by passing deionized water through the column at 10°–25° C.;

(4) selectively displacing one amino acid by adding deionized water under low pressure and at a selected elevated temperature and collecting the desired amino acid in the eluate.

When it is desired to separate and recover two or more amino acids, a different, higher temperature is selected for displacing the second amino acid and the latter collected in the eluate. Similarly, a still higher temperature is employed to recover a third amino acid. The gradient temperature elution effectively separates the desired amino acid or acids from other organic materials. By the appropriate selection of temperatures, certain materials may be removed at lower temperatures before the amino acid is eluted but generally remain retained on the adsorbent.

For useful separation and recovery of mixtures of amino acids at a selected pH, the pKa's of the acids should be within one unit. If two amino acids have pKa's differing by about two units, it is preferable to adjust the pH of the mobile phase. For amino acids differing in pKa by three or more units, it is preferable to load the mixture onto the column at a pH corresponding to the isoelectric point of one of the acids at which pH the other acid would remain completely ionized and would be found in the percolate. The percolate could be adjusted to the pH of the acid having a pKa differing by three or more units and the acid loaded on a second column. The desired amino acids would be recovered from each of the columns by gradient temperature elution with deionized water as above described.

The adsorbent to be employed in the practice of the present invention is non-ionic. Suitable adsorbent polymers are cross-linked copolymers of styrene-divinylbenzene or halogenated, cross-linked copolymers of styrene-divinylbenzene. A preferred adsorbent polymer is "Sepabeads SP207", a brominated styrene-divinylbenzene copolymer available commercially and manufactured by Mitsubishi Chemical Industries, Limited. Other suitable polymers are Diaion HP-20, HP-30, HP-40 polymers (styrene-divinylbenzene copolymers, Mitsubishi Chemical Industries, Ltd.). Less preferred are Amberlite XAD-2 and XAD-4 (styrene-divinylbenzene copolymers, Rohm and Haas Co.). The latter resins are more useful in the purification of a single phenylalanine type amino acid rather than in the separation of mixtures of such acids.

The elution is carried out employing deionized water as eluant and employing low pressure.

The pressure employed is in the range of 3 to 10 pounds per square inch (3–10 psi). By utilizing the pressure, degassing of the trapped air when the column is heated may be avoided and a smoother elution may be carried out. Application of pressure is preferably carried out employing an inert gas such as nitrogen.

The elution temperature for the separation of the amino acids is carried out in the range of from about 50° to 90° C. The initial removal of salts and highly hydrophilic organic impurities is carried out in the temperature range of 10° to 25° C.

The separated amino acids are recovered from the respective eluates by concentrating the aqueous solution, preferably under reduced pressure and then cooling to effect crystallization.

The following examples illustrate the invention but are not to be construed as limiting:

EXAMPLE I

α-Methyldopa

The α-methyldopa filtrate employed was that arising from the hydrolysis of L-α-acetamido-α-vanillylpropionitrile with hydrochloric acid in a manner similar to that described in U.S. Pat. No. 3,366,679.

About 500 milliliters of methyldopa filtrate at pH 4.5–5.0 from the hydrolysis of the nitrile precursor and containing 10–12 grams/liter of α-methyldopa was loaded onto a column containing approximately 300 milliliters of SP-207 resin at a rate of about 2 bed volumes per hour (2 BV/hr) to obtain a loading of about 20 milligrams of α-methyldopa per gram of wet resin. During this operation high levels of inorganic salts and hydrophilic impurities were obtained in the percolate and were discarded.

Following the loading, 250 milliliters of deionized water was applied at ambient temperature at a rate of 2.5 BV/hr to displace and wash the remaining inorganic salts and hydrophilic organic impurities from the column.

After the completion of the displacement and wash, the resin column was heated to about 60° C. and pressurized to approximately 10 psi. Hot (60°–65° C.) deionized water was applied to the column under a pressure of 10 psi at a rate of 2 BV/hr to elute the α-methyldopa product. About 600 milliliters of eluate consisting of fractions which were shown by a high pressure liquid chromatogram (HPLC) were collected. The eluate contained about 95 percent of the methyldopa adsorbed onto the column. The eluate was then concentrated tenfold under vacuum and cooled to 5°–10° C. to effect crystallization. The product was isolated by filtration, washed with cold (5°–10° C.) deionized water and dried at 40° C./25 inches Hg to about 85–90 percent of a product of m.p. 292°–29° C. and assaying ca. 99.8% by USP methods.

The results of six such operations may be seen in Table I.

EXAMPLE II

Levodopa

The levodopa filtrate obtained for this example was that remaining after removal of the bulk of the desired levodopa following hydrochloric acid hydrolysis of N-acetyl-4-acetoxy-3-methoxyphenylalanine. The N-acetyl-4-acetoxy-3-methoxyphenylalanine is obtained by acetylating 3-(4-hydroxy-3-methoxyphenyl) alanine which in turn is obtained by the hydrolysis of vanillylhydantoin under alkaline conditions.

In an operation carried out in a manner similar to that described in Example I, 100 milliliters of an aqueous solution containing 10 grams/liter of levodopa was adjusted to a pH of 5.0 and loaded onto a column containing approximately 300 milliliters of SP-207 resin at a rate of about 2 BV/hr. Thereafter, 80 milliliters of deionized water was applied at a rate of 2.5 BV/hr to wash the impurities from the column.

Hot (60°–65° C.) deionized water was then applied to the column at a pressure of 3–4 psi at a rate of 2 BV/hr to elute the levodopa from the column. Approximately 100 milliters of eluate was concentrated to dryness (under vacuum) to obtain 100 percent yield of levodopa of 100 percent purity as determined by USP methods.

EXAMPLE III

"(3-O-Methyl-α-methyldopa)"

3-(4-Hydroxy-3-methoxyphenyl)-2-methylalanine

In an operation carried out in a manner similar to that described in the preceding examples, 300 milliliters of an aqueous solution resulting from the hydrolysis of the nitrile and containing about 10 grams/liter of 3-O-methyl-α-methyldopa was loaded onto a column containing about 300 milliliters of SP-207 resin at a rate of about 2 BV/hr.

After completion of the loading, the column was washed and thereafter the column pressurized (10 psi) and hot (90° C.) deionized water applied to elute the amino acid and recover it in the eluate. The latter was concentrated under vacuum to dryness to obtain an 85 percent yield of 3-O-methyl-α-methyldopa of 99.8 percent purity as determined by USP methods.

EXAMPLE IV

"3-O-Methyldopa"

3-(4-Hydroxy-3-methoxyphenyl)alanine

In an operation carried out in a manner similar to that of the preceding examples, 300 milliliters of an aqueous solution containing about 10 grams/liter of 3-O-methyldopa was loaded onto a column containing about 300 milliliters of SP-207 resin at a rate of about 2 BV/hour.

TABLE I

| | | | Quality of Product | | | | |
| --- | --- | --- | --- | --- | --- | --- | --- |
| RUN | YIELD Isolated Product | KF (10-13%*) | ASSAY (98-101%)* | MP (>289)* | ROTATION (−25° to −28°)* | UV (Conforms)* | IC (Conforms)* |
| 1 | 91.2% | 11.9% | 99.8% | 293° | −26° | Conforms | Conforms |
| 2 | 91.2% | 11.8% | 99.8% | 292° | −26° | " | " |
| 3 | 87.5% | 11.6% | 99.8% | 292° | −26° | " | " |
| 4+ | 85.6% | 11.6% | 99.8% | 293° | −26° | — | " |
| 5 | 87.7% | 11.8% | 100.2% | 293° | −26° | Conforms | " |
| 6 | 91.0% | 11.7% | 99.9% | 292° | −26° | " | " |

*Specification
+Insufficient sample for UV analysis

After completion of the loading, the column was washed, thereafter pressurized (3-4 psi) and deionized water at a temperature of about 80° C. applied to elute 3-O-methyldopa. The eluate was concentrated under vacuum to dryness to obtain a 98 percent yield of the desired 3-(4-hydroxy-3-methoxyphenyl)alanine of 99.8 percent purity.

EXAMPLE V

Separation of α-Methyldopa and 3-O-methyl-α-methyldopa

A portion (300 milliliters) of the filtrate from the hydrolysis of DL-α-acetamido-α-vanillylpropionitrile at a PH of 4.5–5.0 and containing 10 grams/liter of α-methyldopa and 5 grams/liter of 3-O-methyl-α-methyldopa was loaded on a colum of approximately 300 milliliters of SP-207 resin at a rate of about 2 BV/hr. Following the loading, about 250 milliliters of deionized water was applied in the manner previously described at ambient temperature to wash soluble impurities.

Thereafter, at pressure (3-4 psi) deionized water of temperature 60° C. was applied at a rate of about 2 BV/hr to recover α-methyldopa in the eluate. Then water at 90° C. was applied to obtain 3-O-methyl-α-methyldopa in the eluate. The aqueous eluates were concentrated under reduced pressure to dryness to obtain α-methyldopa in a yield of about 95 percent and 3-O-methyl-α-methyldopa in a yield of about 90 percent. The purity of each was greater than 98 percent as determined by USP methods.

EXAMPLE VI

Isolation of Tyrosine from Protein Hydrolysate 240 grams of casein is refluxed for 4 hours with 2.5 liters of 6N hydrochloric acid. At the end of this period, the solution is evaporated to dryness under reduced pressure, the syrupy residue taken up in 1.5 liters of water and the resulting mixture filtered to remove the insoluble humin.

The filtrate is adjusted to pH of 5 loaded onto a column containing approximately 300 milliliters of SP-207 resin at a rate of about 2 bed volumes per hour (2 BV/hour). The percolate containing inorganic salts and hydrophilic impurities are discarded.

250 milliliters of deionized water then is applied to the column at ambient temperature at a rate of 2.5 BV/hour to displace and wash the remaining inorganic salts and hydrophilic organic impurities from the column.

The resin column is then heated to about 60° C. and pressurized to approximately 10 psi. Hot (60°-65° C.) deionized water then is applied to the column under a pressure of 3-10 psi at a rate of 2 BV/hour to elute the desired tyrosine which is recovered from the eluate by concentrating the latter under reduced pressure and allowing the concentrated solution to stand at ambient temperature. The tyrosine then separates as crystals.

EXAMPLE VII

Isolation of Tyrosine and Phenylalanine from Protein Hydrolysate

In an operation carried out in a manner similar to that described in Example VI, 240 grams of ovalbumin is first refluxed for 4 hours with 2.5 liters of 6N hydrochloric acid, the resulting solution evaporated to a syrupy residue under reduced pressure, the residue then taken up in 1.5 liters of water and finally, the resulting mixture filtered.

The filtrate is brought to pH 5 with alkali and loaded onto a column containing SP-207 resin. After completion of the loading, 250 milliliters of deionized water is applied to wash and displace water-soluble impurities.

The resin column is then heated to about 60° C. and pressurized to about 10 psi and hot (60°-65° C.) deionized water applied to the column under a pressure of 3-10 psi at a rate 2 BV/hour to elute the tyrosine which may be recovered as previously described.

The temperature of the resin column is then increased to 90° C. while the pressure is maintained at about 10 psi. Hot (90°-95° C.) deionized water is applied to the column under a pressure of 3-10 psi at a rate of 2 BV/hour to elute the phenylalanine. The latter is recovered from the eluate by concentrating the eluate under reduced pressure and letting the solution stand at ambient temperature to allow the phenylalanine to separate as crystals.

EXAMPLE VIII

Separation of Levodopa and "3-O-Methyldopa"

A filtrate obtained during the preparation of levodopa by the hydrolysis of N-acetyl-4-acetoxy-3-methoxyphenylalanine and containing some dissolved levodopa and 3-O-methyldopa is adjusted to pH 5 and loaded on a column in the manner described in Example II, and the column then is washed with deionized water.

Separation is effected by first heating the column to about 60° C. and applying hot (60°-65° C.) deionized water at a pressure of 3-4 psi at 2 BV/hr whereupon levodopa is obtained in the eluate and may be recovered as previously described. The temperature of the column is then increased to about 80° C. and hot (80°-85° C.) deionized water applied to elute 3-O-methyldopa. The latter may be recovered as previously described.

EXAMPLE IX

Isolation of Levodopa from Fermentation Broth

L-Dopa (levodopa) is produced from L-tyrosine by the action of *Vibrio tyrosinaticus* ATCC 19,378 in an aqueous nutrient medium containing assimilable sources of carbon, nitrogen and inorganic salts at temperatures of 22° to 37° C. in a manner similar to that described in U.S. Pat. No. 3,703,439.

The fermentation broth containing levodopa is first filtered through supercel and the filtrate adjusted by concentrating or diluting with water as necessary to obtain an aqueous solution containing about 10 grams/liter of levodopa. The pH of the solution is adjusted to about 5.0 and the solution is loaded onto a column containing approximately 300 milliliters of SP-207 resin at a rate of 2 BV/hr. Thereafter, 80 milliliters of deionized water is applied at a rate of 2.5 BV/hr to wash the impurities from the column.

Levodopa is then eluted from the column by applying hot (60°-65° C.) deionized water at a pressure of 3-4 psi at a rate of 2 BV/hr. The eluate is concentrated under vacuum to obtain substantially pure levodopa.

EXAMPLE X

Isolation of L-Phenylalanine from Fermentation Broth

L-Phenylalanine is produced from L-tyrosine by cultivating under submerged, aerobic conditions at a PH from about 6.0 to about 8.0, *E. coli*, ATCC 13281, in an aqueous nutrient medium comprising a source of carbon, a source of nitrogen, and a source of magnesium, potassium, and trace metals in the presence of from about 10 to about 200 milligrams of L-tyrosine per liter of nutrient medium.

The solution is concentrated under vacuum to obtain a solution containing about 10 grams/liter of phenylalanine. The solution is loaded onto a column containing about 300 milliliters of SP-207 resin at a rate of about 2 BV/hr. Thereafter, the column is washed, then pressurized (about 10 psi) and hot (90° C.) deionized water applied to elute the phenylalanine. The eluate is concentrated under reduced pressure and the phenylalanine allowed to separate as crystals.

What is claimed is:

1. A method for recovering in substantially pure form an amino acid having the formula

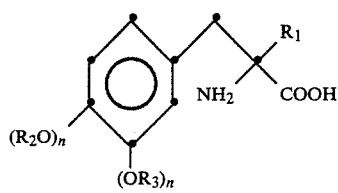

wherein $R_1$, $R_2$ and $R_3$ are independently hydrogen, lower alkyl, lower haloalkyl and aryl and each n independently is 0 or 1, from an aqueous mixture containing at least one amino acid conforming to the general formula and which contains other organic and inorganic matter including other amino acids, protein hydrolysates, organic compounds and inorganic salts, comprising
   (1) adjusting the pH of the aqueous mixture to a pH at or near the isoelectric pH of the desired amino acid;
   (2) loading the mixture on a column of a non-ionic polymer resin of styrene-divinylbenzene copolymer and allowing the aqueous solution to percolate through the column;
   (3) displacing the entrained or adsorbed inorganic salts by passing deionized water through the column at 10°–25° C.
   (4) selectively displacing one amino acid by adding deionized water under low pressure and at a selected elevated temperature, said temperature being at least 50° C., and collecting the desired amino acid in the eluate.

2. A process according to claim 1 wherein more than one amino acid of the desired structure is recovered which comprises the additional steps of
   (5) displacing the second amino acid by increasing the temperature of the column to a selected temperature higher than the temperature employed for the first elution but no higher than 95° C. and adding deionized water at said elevated temperature and collecting the eluate; and
   (6) optionally repeating said process at increasing elevated temperatures for each desired amino acid.

3. A process according to claim 1 or 2 wherein the desired amino acid is recovered from the respective eluates by concentrating and cooling to effect crystallization.

4. A process according to claim 1 in which the amino acid obtained is L-methyldopa.

5. A process according to claim 1 in which the amino acid recovered is L-dopa.

6. A process according to claim 1 in which the aqueous mixture is a production stream for a chemical synthetic process for the desired amino acid.

7. A process according to claim 1 in which the aqueous mixture is a mixture of a fermentation process.

8. A process according to claim 1 in which the aqueous mixture is a mixture from a peptide or protein hydrolysis.

9. A process according to claim 1 wherein the non-ionic polymer resin is a cross-linked copolymer of styrene-divinylbenzene or halogenated cross-linked copolymer of styrene-divinylbenzene.

10. A method for recovering L-methyldopa in substantially pure form from an aqueous mixture containing at least one other α-amino acid and which contains other organic and inorganic matter including other amino acids, protein hydrolysates, organic compounds and inorganic salts comprising
    (1) adjusting the pH of the aqueous mixture to a pH at or near the isoelectric pH of L-methyldopa;
    (2) loading the mixture on a column of a non-ionic polymer resin and allowing the aqueous solution to percolate through the column;
    (3) displacing the entrained or adsorbed inorganic salts by passing deionized water through the column at 10°–25° C.;
    (4) selectively displacing L-methyldopa by adding deionized water under low pressure and at an elevated temperature of about 60° C. and collecting the desired amino acid in the eluate.

11. A method for recovering L-dopa in substantially pure form from an aqueous mixture containing at least one other α-amino acid and which contains other organic and inorganic matter including other amino acids, protein hydrolysates, organic compounds and inorganic salts, comprising
    (1) adjusting the pH of the aqueous mixture to a pH at or near the isolectric pH of L-dopa;
    (2) loading the mixture on a column of a non-ionic polymer resin and allowing the aqueous solution to percolate through the column;
    (3) displacing the entrained or adsorbed inorganic salts by passing deionized water through the column at 10°–25° C.;
    (4) selectively displacing L-dopa by adding deionized water under low pressure and at an elevated temperature of about 60° C. and collecting the desired amino acid in the eluate.

12. A process according to claim 1 in which the amino acid is 3-(4-hydroxy-3-methoxyphenyl)-2-methylalanine.

13. A process according to claim 1 in which the amino acid is 3-(4-hydroxy-3-methoxyphenyl)alanine.

14. A process according to claim 2 in which the amino acids are α-methyldopa and 3-O-methyl-α-methyldopa.

* * * * *